US012279869B2

United States Patent
Hakoshima

(10) Patent No.: US 12,279,869 B2
(45) Date of Patent: Apr. 22, 2025

(54) EVALUATION APPARATUS, EVALUATION METHOD, AND NON-TRANSITORY STORAGE MEDIUM

(71) Applicant: JVCKENWOOD Corporation, Yokohama (JP)

(72) Inventor: Shuji Hakoshima, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 675 days.

(21) Appl. No.: 17/468,726

(22) Filed: Sep. 8, 2021

(65) Prior Publication Data

US 2021/0401336 A1 Dec. 30, 2021

Related U.S. Application Data

(63) Continuation of application No. PCT/JP2019/044446, filed on Nov. 12, 2019.

(30) Foreign Application Priority Data

Mar. 22, 2019 (JP) .................................. 2019-054142

(51) Int. Cl.
*A61B 5/16* (2006.01)
*A61B 5/00* (2006.01)

(52) U.S. Cl.
CPC .............. *A61B 5/163* (2017.08); *A61B 5/168* (2013.01); *A61B 5/7425* (2013.01)

(58) Field of Classification Search
CPC .......... A63B 3/024; A63B 5/168; A63B 5/163
See application file for complete search history.

(56) References Cited

U.S. PATENT DOCUMENTS

2013/0155376 A1  6/2013 Huang et al.
2017/0224210 A1* 8/2017 Mori .................... A61B 5/7275

FOREIGN PATENT DOCUMENTS

| JP | 2014-18484 | 2/2014 |
| JP | 2014-18565 | 2/2014 |
| JP | 2015-502238 | 1/2015 |
| JP | 2016-171849 | 9/2016 |

OTHER PUBLICATIONS

International Search Report and Written Opinion for International Application No. PCT/JP2019/044446 mailed on Jan. 7, 2020, 10 pages.

* cited by examiner

*Primary Examiner* — Benjamin S Melhus
(74) *Attorney, Agent, or Firm* — Amin, Turocy & Watson, LLP

(57) ABSTRACT

An evaluation apparatus includes a display; a gaze point detection unit configured to detect a position of a gaze point of a subject; a display controller configured to display an evaluation image including a main target image, sub target images, and an instruction information to gaze at the main target image; a region setting unit configured to set determination regions for the sub target images; a determination unit configured to determine whether the gaze point is present in the determination regions based on the position of the gaze point; an arithmetic unit configured to measure an arrival time from a predetermined time to a first arrival time of the gaze point at the determination regions based on a result of the determination unit; and an evaluation unit configured to obtain an evaluation data of the subject based on an average or a total value of the arrival times.

6 Claims, 7 Drawing Sheets

EVALUATION APPARATUS, EVALUATION METHOD, AND NON-TRANSITORY STORAGE MEDIUM

CROSS-REFERENCE TO RELATED APPLICATIONS

This application is a Continuation of PCT International Application No. PCT/JP2019/044446 filed on Nov. 12, 2019 which claims the benefit of priority from Japanese Patent Application No. 2019-054142 filed on Mar. 22, 2019, the entire contents of which are incorporated herein by reference.

FIELD

The present disclosure relates to an evaluation apparatus, an evaluation method, and a non-transitory storage medium.

BACKGROUND

In recent years, the number of persons with developmental disorders tends to increase. It is known that an early detection of the developmental disorders and a start of a medical treatment thereof reduces symptoms of the developmental disorders to increase an effect to achieve social adjustment. Therefore, an evaluation apparatus capable of evaluating a probability of the developmental disorders objectively and effectively is required.

Japanese Laid-open Patent Publication No. 2016-171849 describes a method of evaluating a probability of Attention Deficit Hyperactivity Disorder (ADHD) among the developmental disorders. In this method, a first image is displayed in a center of a display, a second image is displayed around the first image, an instruction to gaze at the first image is given to a subject, a gaze point of the subject on the display is detected, and the probability of ADHD is evaluated based on a retention time in which the gaze point is retained in a region for each of the images.

A subject with ADHD tends to frequently move a gaze point due to hyperactivity or impulsivity, for example. In the method described in Japanese Laid-open Patent Publication No. 2016-171849, it is possible to indirectly evaluate a movement of the gaze point by comparing the retention time of the gaze point in the image for which the gaze instruction is given and the retention time of the gaze point in the other image. Therefore, there is a need to perform an evaluation that is directly suitable for characteristics of ADHD.

SUMMARY

An evaluation apparatus, an evaluation method, and a non-transitory storage medium are disclosed.

According to one aspect, there is provided an evaluation apparatus comprising: a display; a gaze point detection unit configured to detect a position of a gaze point of a subject; a display controller configured to display, on the display, an evaluation image including a main target image, multiple sub target images, and an instruction information for instructing the subject to gaze at the main target image; a region setting unit configured to set multiple determination regions for the multiple sub target images respectively; a determination unit configured to determine whether the gaze point is present in each of the multiple determination regions based on the detected position of the gaze point; an arithmetic unit configured to measure an arrival time from a predetermined time to a first arrival time of the gaze point at each of the multiple determination regions based on a determination result of the determination unit; and an evaluation unit configured to obtain an evaluation data of the subject based on an average value or a total value of all of the arrival times for all of the multiple determination regions.

According to one aspect, there is provided an evaluation method comprising: detecting a position of a gaze point of a subject; displaying, on a display, an evaluation image including a main target image, multiple sub target images, and an instruction information for instructing the subject to gaze at the main target image; setting multiple determination regions for the multiple sub target images respectively; determining whether the gaze point is present in each of the multiple determination regions based on the detected position of the gaze point; measuring an arrival time from a predetermined time to a first arrival time of the gaze point at each of the multiple determination regions based on a determination result of the determining; and obtaining an evaluation data of the subject based on an average value or a total value of all of the arrival times for all of the multiple determination regions.

According to one aspect, there is provided a non-transitory storage medium that stores an evaluation program that causes a computer to execute: a process of detecting a position of a gaze point of a subject; a process of displaying, on a display, an evaluation image including a main target image, multiple sub target images, and an instruction information for instructing the subject to gaze at the main target image; a process of setting multiple determination regions for the multiple sub target images respectively; a process of determining whether the gaze point is present in each of the multiple determination regions based on the detected position of the gaze point; a process of measuring an arrival time from a predetermined time to a first arrival time of the gaze point at each of the multiple determination regions based on a determination result of the determining; and a process of obtaining an evaluation data of the subject based on an average value or a total value of all of the arrival times for all of the multiple determination regions.

The above and other objects, features, advantages and technical and industrial significance of this application will be better understood by reading the following detailed description of presently preferred embodiments of the application, when considered in connection with the accompanying drawings.

DETAILED DESCRIPTION OF THE PREFERRED EMNODIMENTS

Embodiments of an evaluation apparatus, an evaluation method, and an evaluation program according to the present disclosure will be described below based on the drawings. The present disclosure is not limited by the embodiments below. Further, structural elements in the embodiments described below include one that can easily be replaced by a person skilled in the art or one that is practically identical.

In the description below, the three-dimensional global coordinate system is set to describe positional relationships between components. A direction parallel to a first axis of a predetermined plane will be referred to as an X-axis direction, a direction parallel to a second axis of the predetermined plane perpendicular to the first axis will be referred to as an Y-axis direction, and a direction parallel to a third axis perpendicular to each of the first axis and the second axis will be referred to as a Z-axis direction. The predetermined plane includes an XY plane.

Evaluation Apparatus

Figure 1:
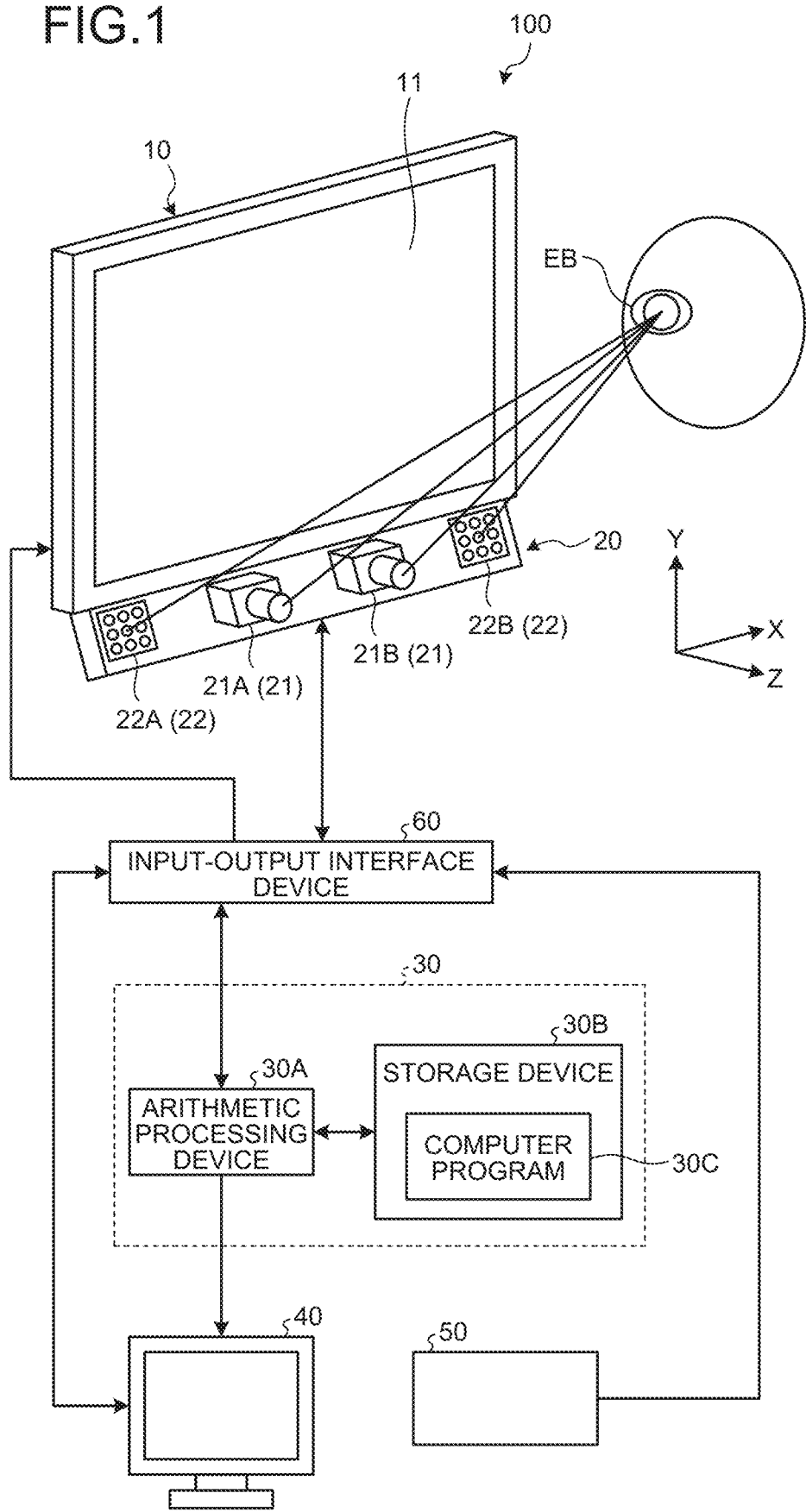
FIG. 1 is a diagram schematically illustrating an example of an evaluation apparatus according to the present embodiment.

FIG. 1 is a diagram schematically illustrating an example of an evaluation apparatus 100 according to the present embodiment. The evaluation apparatus 100 according to the present embodiment detects a line of sight of a subject, and evaluates Attention Deficit Hyperactivity Disorder (ADHD) by a detection result. The evaluation apparatus 100 is able to detect the line of sight of the subject by various methods, such as a method of detecting the line of sight based on a position of a pupil of the subject and a position of a corneal reflection image or a method of detecting the line of sight based on a position of an inner corner of an eye of the subject and a position of an iris of the subject, for example.

As illustrated in FIG. 1, the evaluation apparatus 100 includes a display device 10, an image acquisition device 20, a computer system 30, an output device 40, an input device 50, and an input-output interface device 60. The display device 10, the image acquisition device 20, the computer system 30, the output device 40, and the input device 50 perform data communication via the input-output interface device 60. Each of the display device 10 and the image acquisition device 20 includes a driving circuit (not illustrated).

The display device 10 includes a flat panel display, such as a liquid crystal display (LCD) or an organic electroluminescence display (OLED). In the present embodiment, the display 10 includes a display 11. The display 11 displays information, such as images. The display 11 is substantially parallel to the XY plane. The X-axis direction is a horizontal direction of the display 11, the Y-axis direction is a vertical direction of the display 11, and the Z-axis direction is a depth direction perpendicular to the display 11. The display device 10 may be a head mounted display device. If the display device 10 is a head mounted display device, a configuration like the image acquisition device 20 is arranged in a head mounted module thereof.

The image acquisition device 20 acquires image data of left and right eyeballs EB of the subject, and transmits the acquired image data to the computer system 30. The image acquisition device 20 includes an imaging device 21. The imaging device 21 captures images of the left and right eyeballs EB of the subject and acquires the image data. The imaging device 21 includes various cameras for the methods of detecting the line of sight of the subject. For example, if the method of detecting the line of sight based on the position of the pupil of the subject and the position of the corneal reflection image is adopted, the imaging device 21 includes an infrared camera, an optical system capable of transmitting near-infrared light at a wavelength of 850 nm, and an imaging element capable of receiving the near-infrared light, for example. Further, for example, if the method of detecting the line of sight based on the position of the inner corner of the eye of the subject and the position of the iris of the subject is adopted, the imaging device 21 includes a visible light camera. The imaging device 21 outputs a frame synchronous signal. A cycle of the frame synchronous signal may be, for example, 20 milliseconds (msec), but is not limited thereto. The imaging device 21 may be configured as, for example, a stereo camera including a first camera 21A and a second camera 21B, but is not limited thereto.

Furthermore, for example, if the method of detecting the line of sight based on the position of the pupil of the subject and the position of the corneal reflection image is adopted, the image acquisition device 20 includes a lighting device 22 that illuminates the eyeballs EB of the subject. The lighting device 22 includes a light emitting diode (LED) light source for example, and is able to emit near-infrared light at a wavelength of 850 nm. Meanwhile, for example, if the method of detecting the line of sight based on the position of the inner corner of the eye of the subject and the position of the iris of the subject is adopted, the lighting device 22 may be omitted. The lighting device 22 emits detection light in synchronization with the frame synchronous signal of the imaging device 21. The lighting device 22 may include, for example, a first light source 22A and a second light source 22B, but is not limited thereto.

The computer system 30 integrally controls an operation of the evaluation apparatus 100. The computer system 30 includes an arithmetic processing device 30A and a storage device 30B. The arithmetic processing device 30A includes a microprocessor, such as a central processing unit (CPU). The storage device 30B includes a memory, such as a read only memory (ROM) and a random access memory (RAM), or a storage. The arithmetic processing device 30A performs an arithmetic process in accordance with a computer program 30C that is stored in the storage device 30B.

The output device 40 includes a display device, such as a flat panel display. Meanwhile, the output device 40 may include a printing device. The input device 50 generates input data by being operated. The input device 50 includes a keyboard or a mouse for a computer system. Meanwhile, the input device 50 may include a touch sensor that is arranged on a display of the output device 40 that is a display device.

In the evaluation apparatus 100 according to the present embodiment, the display device 10 and the computer system 30 are separate devices. Meanwhile, the display device 10 and the computer system 30 may be integrated. For example, the evaluation apparatus 100 may include a tablet personal computer. In this case, the display device, the image acquisition device, the computer system, the input device, the output device, and the like may be mounted on the tablet personal computer.

Figure 2:
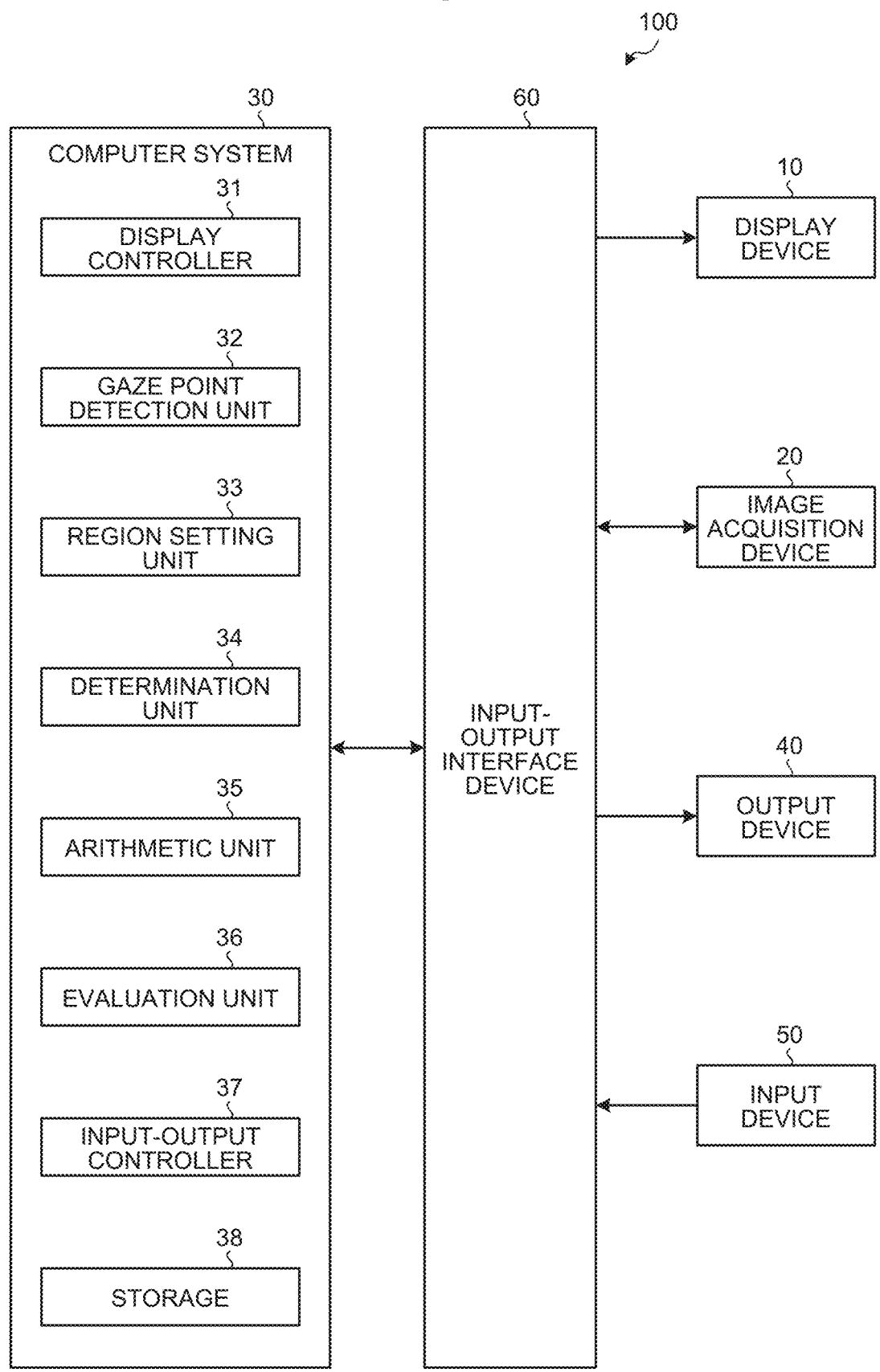
FIG. 2 is a functional block diagram illustrating an example of the evaluation apparatus.

FIG. 2 is a functional block diagram illustrating an example of the evaluation apparatus 100. As illustrated in FIG. 2, the computer system 30 includes a display control unit 31, a gaze point detection unit 32, a region setting unit 33, a determination unit 34, an arithmetic unit 35, an evaluation unit 36, an input-output control unit 37, and a storage 38. Functions of the computer system 30 are implemented by the arithmetic processing device 30A and the storage device 30B (see FIG. 1). Meanwhile, a part of the functions of the computer system 30 may be arranged outside the evaluation apparatus 100.

The display control unit 31 displays an instruction information (described later) on the display 11, and thereafter displays an evaluation image on the display 11. In the present embodiment, the evaluation image is an image including a main target image and a sub target image. Further, the instruction information is an information to instruct the subject to gaze at the main target image in the evaluation image. The display control unit 31 does not have to always display the instruction information. Further, the display control unit 31 may display the instruction information and the evaluation image simultaneously. The main target image and the sub target image are arranged independent of each other. The display control unit 31 displays different images as the main target image and the sub target image, for example. Meanwhile, the display control unit 31 may display the same image as the main target image and the sub target image. The display control unit 31 displays the evaluation image on the display such that the main target image and the sub target image are displayed with a time lag. For example, the display control unit 31 changes the evaluation image from a state in which the sub target images can hardly be recognized by the subject to a state in which the sub target images can easily be recognized by the subject. Here, the state in which the sub target image can hardly be recognized by the subject is, for example, a state with high transparency, a state with low brightness, a state with low saturation, a state with a small size, or the like. In contrast, the state in which the sub target image can easily be recognized by the subject is, for example, a state with low transparency, a state with high brightness, a state with high saturation, a state with a large size, or the like. Therefore, the display control unit 31 is able to change the evaluation image from the state in which the sub target image can hardly be recognized by the subject to the state in which the sub target image can easily be recognized by the subject by changing the state of the sub target image by, for example, reducing the transparency of the sub target image, increasing the brightness, increasing the saturation, and increasing the size with time. For example, the display control unit 31 is able to allow the subject to recognize the subject target image with a delay from the main target image, by reducing the transparency of the sub target image with time. The display control unit 31 is able to display the above-described evaluation image and the above-described instruction information as an evaluation image on the display 11 for example. However, a display mode is not limited to the evaluation image, and may be a still image. The display control unit 31 may display multiple sub target images. Further, the display control unit 31 may display the main target image and the sub target image simultaneously without a time lag. Furthermore, the display control unit 31 may display an identical image as the main target image and the sub target image, and display a main target object for the main target image and a sub target object for the sub target image.

The gaze point detection unit 32 detects a positional data of the gaze point of the subject. In the present embodiment, the gaze point detection unit 32 detects a line-of-sight vector of the subject defined by the three-dimensional global coordinate system, based on the image data of the left and right eyeballs EB of the subject acquired by the image acquisition device 20. The gaze point detection unit 32 detects, as the positional data of the gaze point of the subject, a positional data of an intersection of the detected line-of-sight vector of the subject and the display 11 of the display device 10. In other words, in the present embodiment, the positional data of the gaze point is the positional data of the intersection of the line-of-sight vector of the subject defined by the three-dimensional global coordinate system and the display 11 of the display device 10. The gaze point detection unit 32 detects the positional data of the gaze point of the subject for each defined sampling cycle. The sampling cycle may be a cycle (for example, every 20 msec) of the frame synchronous signal output from the imaging device 21.

The region setting unit 33 sets a determination region for the sub target image on the display 11. If the multiple sub target images are displayed on the display 11, the region setting unit 33 sets a determination region for each of the multiple sub target images. In the present embodiment, each of the determination regions set by the region setting unit 33 is not displayed on the display 11 in principle. Meanwhile, each of the determination regions may be displayed on the display 11 under a control of the display control unit 31, for example. Furthermore, the region setting unit 33 is able to set a specific region for the main target image on the display 11.

The determination unit 34 determines whether the gaze point is present in the determination regions based on the positional data of the gaze point, and outputs a determination result as a determination data. The determination unit 34 determines whether the gaze point is present in the determination regions for each prescribed determination cycle. The determination cycle may be, for example, a same cycle as the cycle (for example, every 20 msec) of the frame synchronous signal output from the imaging device 21. In other words, the determination cycle of the determination unit 34 is the same as the sampling cycle of the gaze point detection unit 32. The determination unit 34 performs determination on the gaze point every time the gaze point detection unit 32 performs sampling of the position of the gaze point. When the multiple determination regions are set, the determination unit 34 is able to determine whether the gaze point is present in each of the multiple determination regions and output a determination data.

The arithmetic unit 35 calculates an arrival time until the gaze point first arrives at the determination region based on the determination data of the determination unit 34. The arrival time indicates a time from a predetermined time to a time at which the gaze point is determined to be first present in the determination region by moving to the determination region. The arithmetic unit 35 includes a timer that measures a time. The arithmetic unit 35 calculates the arrival time by the timer. The arithmetic unit 35 is able to adopt, as the predetermined time as a start point for calculation of the arrival time, a time at which display of the evaluation image is started after the instruction information is provided, for example. Further, when the specific region for the main target image is set, the arithmetic unit 35 may adopt, as the predetermined time, a time at which the gaze point of the subject is first confirmed to be present in the specific region, for example. The arithmetic unit 35 stores the calculated arrival time as an arrival time data in the storage 38. When the multiple determination regions are set, the arithmetic unit 35 is able to calculate the arrival time for each of the determination regions. Meanwhile, the arithmetic unit 35 includes a management timer that manages a reproduction time of the evaluation image.

The evaluation unit 36 obtains an evaluation data of the subject based on the arrival time of the gaze point. The evaluation data includes data for evaluating whether the subject is being able to gaze at the main target image and the sub target image displayed on the display 11.

The input-output control unit 37 acquires data (the image data of the left and right eyeballs EB, the input data, or the like) from at least one of the image acquisition device 20 and the input device 50. Further, the input-output control unit 37 outputs data to at least one of the display device 10 and the output device 40. The input-output control unit 37 may output a task for the subject from the output device 40, such as a speaker.

The storage 38 stores therein the determination data, the arrival time data, and the evaluation data as described above. Further, the storage 38 stores therein an evaluation program that causes a computer to perform a process of detecting the position of the gaze point of the subject, a process of displaying, on the display 11, the evaluation image including the main target image, the sub target image, and the instruction information for instructing the subject to gaze at the main target image, a process of setting the determination region for the sub target image, a process of setting the specific region for the main target image, a process of determining whether the gaze point is present in the determination region based on the position of the detected gaze point, a process of measuring the arrival time from a predetermined time to a first arrival time of the gaze point at the determination region based on a determination result, and a process of obtaining the evaluation data of the subject based on the arrival time.

Evaluation Method

The evaluation method according to the present embodiment will be described below. In the evaluation method according to the present embodiment, the possibility of ADHD of the subject is evaluated by using the evaluation apparatus 100 as described above.

Figure 3:
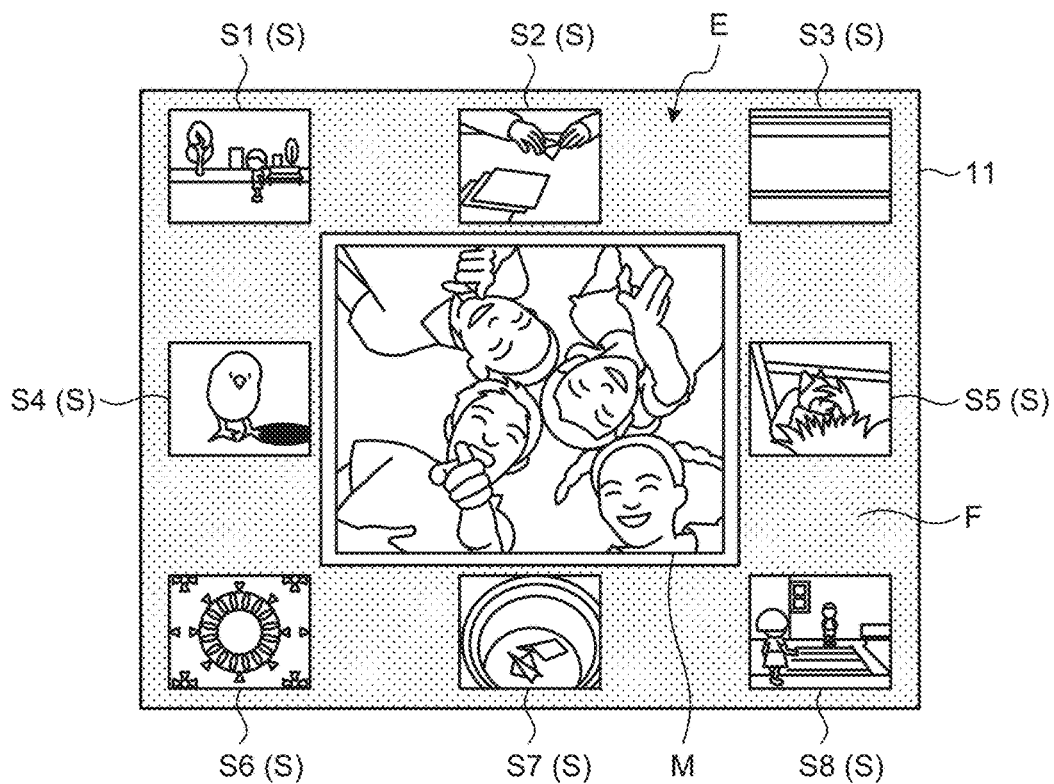
FIG. 3 is a diagram illustrating an example of an evaluation image displayed on a display.

FIG. 3 is a diagram illustrating an example of an evaluation image E displayed on the display 11. As illustrated in FIG. 3, the display control unit 31 displays the evaluation image E including a main target image M and sub target images S on the display 11. The main target image M is arranged in a center of the display 11 and displays multiple persons, for example. The main target image M has, for example, a rectangular shape, but is not limited thereto, and may have a circular shape, another polygonal shape, such as a triangle shape, or other shapes. The sub target images S are arranged in a frame portion F around the main target image M. The sub target images S are arranged at, for example, eight portions in a total, that is, four corner portions of the display 11 and central portions of four sides of the display 11. The main target image M has a larger size than those of the eight sub target images S. Each of the eight sub target images S has the same size. Meanwhile, the display positions and the sizes of the main target image M and the sub target image S, the number of the sub target images S, and the like are not limited to this example. The eight sub target images S are referred to as sub target images S1 to S8 when they are distinguished from one another.

Figure 4:
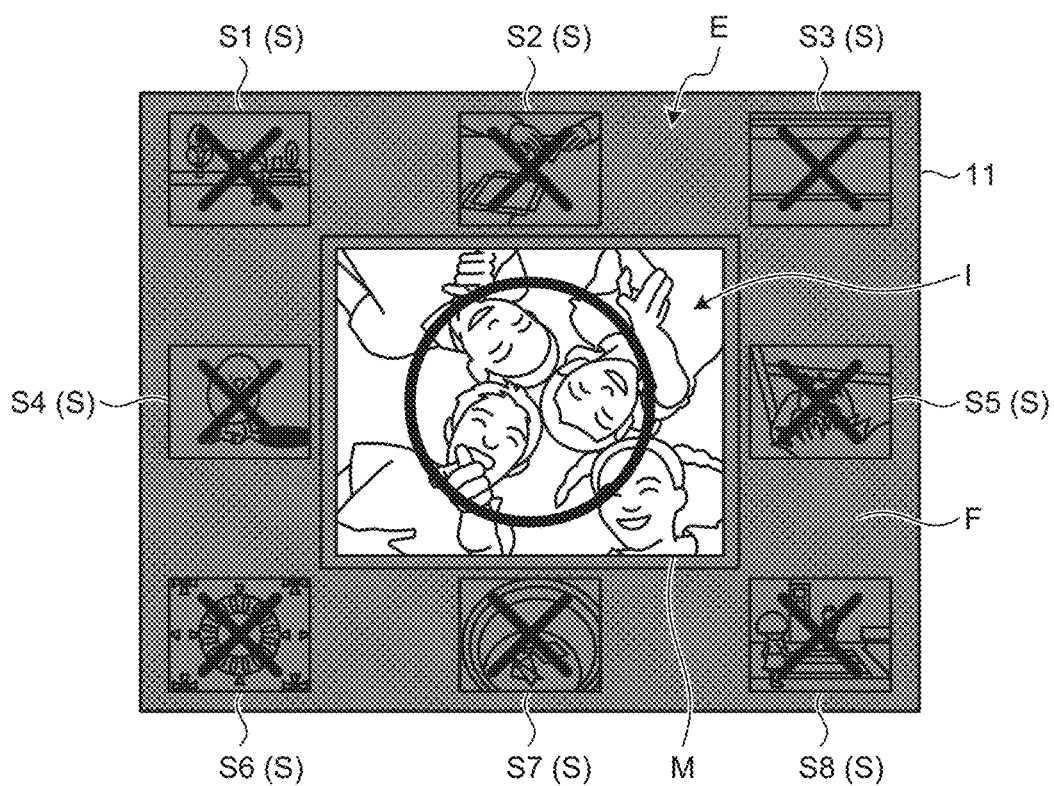
FIG. 4 is a diagram illustrating an example of an instruction information on the display.

FIG. 4 is a diagram illustrating an example of a display of an instruction information I on the display 11. As illustrated in FIG. 4, the display control unit 31 displays, on the display 11, the instruction information I for instructing the subject to gaze at the main target image M in the evaluation image E. In the example illustrated in FIG. 4, the display control unit 31 darkens regions other than the main target image M, displays, as the instruction information I, an index "o" in a portion for the main target image M, and displays indices "x" in portions for the sub target images S. Meanwhile, the instruction information I is not limited to those using the evaluation image E. For example, the display control unit 31 may display an instruction information, such as characters, on the display 11 without displaying the evaluation image E. Further, the input-output control unit 37 may cause a speaker to output a voice, such as "gaze at a central image", for the instruction information I in addition to displaying the instruction information I or instead of displaying the instruction information I. For example, the input-output control unit 37 may cause the speaker to output a voice, such as "gaze at a central image", for the instruction information I, without displaying the instruction information I.

Figure 5:
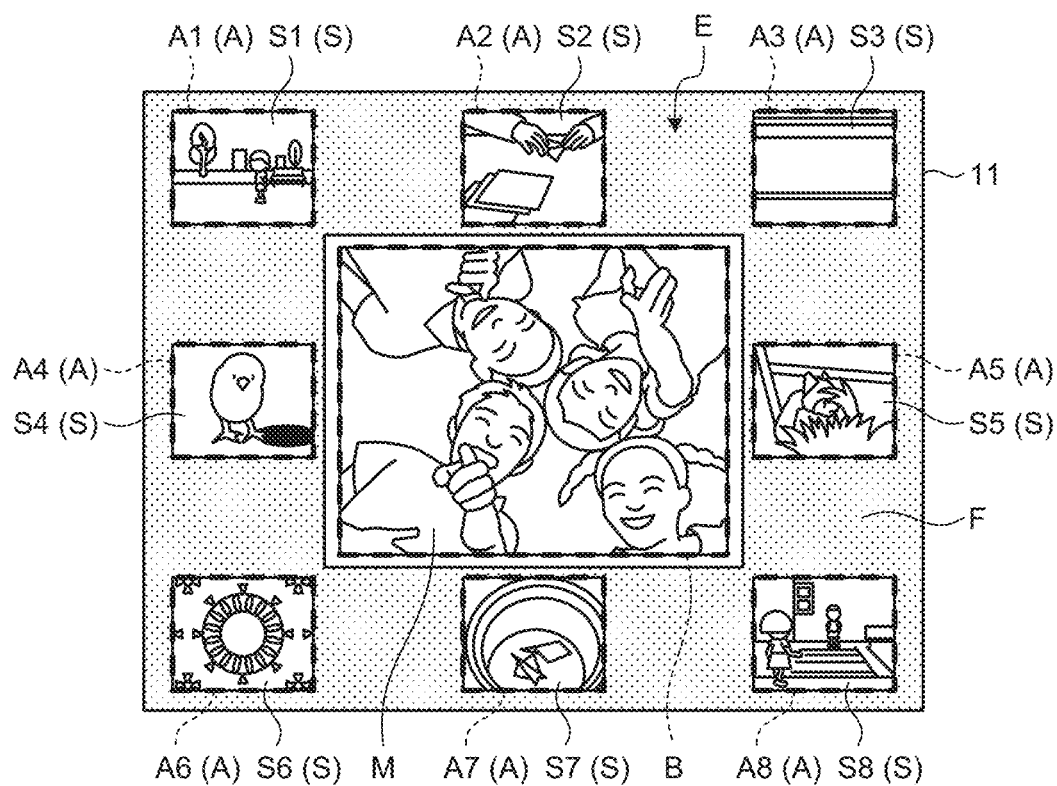
FIG. 5 is a diagram illustrating an example of determination regions set in the display.

FIG. 5 is a diagram illustrating an example of the determination regions set on the display 11. As illustrated in FIG. 5, the region setting unit 33 sets the determination regions for the sub target images S. In the following, the determination regions A for the sub target images S may be referred to as determination regions A1 to A8 when the determination regions are distinguished from one another. The region setting unit 33 sets the determination regions A in ranges that do not overlap with one another. The determination regions A are not displayed on the display 11. Each of the determination regions A has, for example, a rectangular shape, but is not limited thereto, and may have a circular shape, another polygonal shape, such as a triangle shape, or other shapes. Each of the determination regions A may be set so as to entirely include each of the sub target images S or so as to partially include each of the sub target images S. Further, the region setting unit 33 is able to set a specific region B for the main target image M. The region setting unit 33 sets the specific region B in a range that does not overlap with the determination regions A. The specific region B is not displayed on the display 11. The specific region B has, for example, a rectangular shape, but is not limited thereto, and may have a circular shape, another polygonal shape, such as a triangle shape, or other shapes. The specific region B may be set so as to include the entire main target image M or so as to include a part of the main target image M.

Examples of characteristics of ADHD include inattention, hyperactivity, and impulsivity. A subject with ADHD, even when the subject is instructed to gaze at a predetermined region, tends to move a gaze point to a different region other than the predetermined region at an early stage after the start of evaluation, due to hyperactivity or impulsivity, for example. In contrast, a subject without ADHD tends to move a gaze point to a different region other than the predetermined region with a temporal delay after the start of the evaluation or tends not to move the gaze point to other regions. Therefore, in the present embodiment, after giving an instruction to gaze at the main target image M, the sub target images S that attract an attention of the subject are displayed, the arrival time of the first arrival at the determination region A for the sub target image S is measured, and the subject is evaluated based on the measured arrival time.

First, the display control unit 31 displays the evaluation image E on the display 11. The evaluation image E includes, for example, the main target image M and the sub target images S (see FIG. 3). After displaying the evaluation image E, the display control unit 31 displays, on the display 11, the instruction information I for instructing the subject to gaze at the main target image M in the evaluation image E (see FIG. 4). Meanwhile, the display control unit 31 may first display the instruction information I instead of displaying the evaluation image E before displaying the instruction information I.

Figure 6:
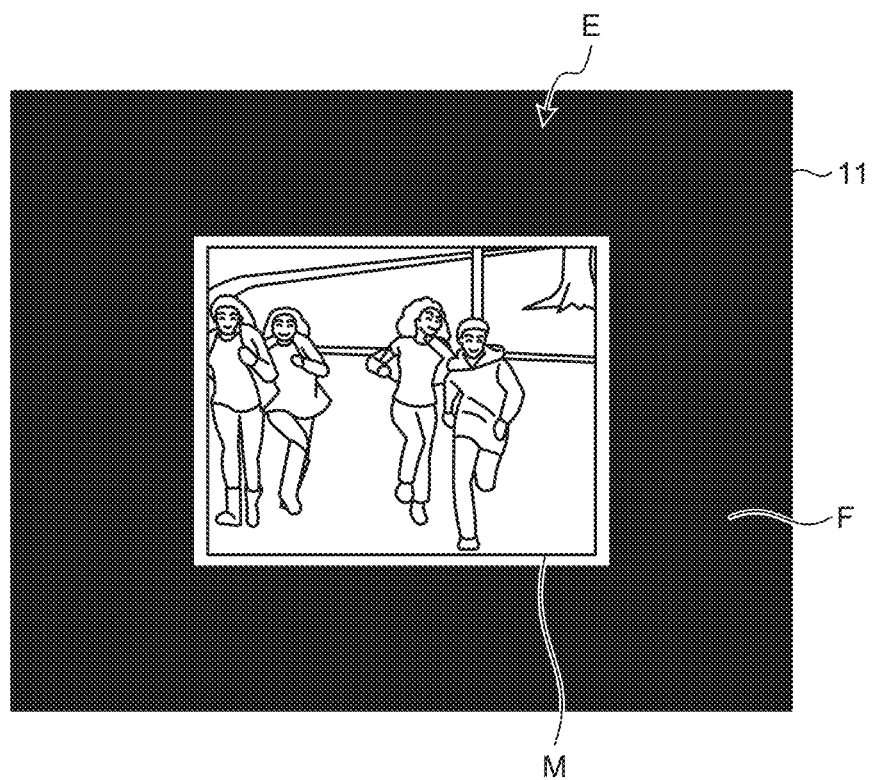
FIG. 6 is a diagram illustrating a display transition of the evaluation image.

Thereafter, the display control unit 31 terminates the display of the instruction information I, and displays the evaluation image E. FIG. 6 to FIG. 10 are diagrams illustrating a display transition of the evaluation image E. First, as illustrated in FIG. 6, the display control unit 31 displays the main target image M in the central portion of the display 11, and, with respect to the sub target images S and the frame portion F, changes the evaluation image E from the state in which the sub target images S can hardly be recognized by the subject to the state in which the sub target images S can easily be recognized by the subject. In the present embodiment, the display control unit 31 reduces the transparency with time for example, but embodiments are not limited thereto, and it may be possible to change the evaluation image E from the state in which the sub target images S can hardly be recognized by the subject to the state in which the sub target images S can easily be recognized by the subject by another method. Specifically, the display control unit 31 first displays the sub target images S and the frame portion F with transparency of 100%. Accordingly, the sub target images S and the frame portion F are not apparently displayed on the display 11. A region for the frame portion F is colored in black, but embodiments are not limited thereto, and may be colored in multiple colors or may be patterned. Further, the region setting unit 33 sets the determinations regions (A1 to A8: see FIG. 5) (not illustrated) for the sub target images S in the evaluation image E. The region setting unit 33 maintains the set determination regions A1 to A8 until a display period of the evaluation image E ends.

Figure 7:
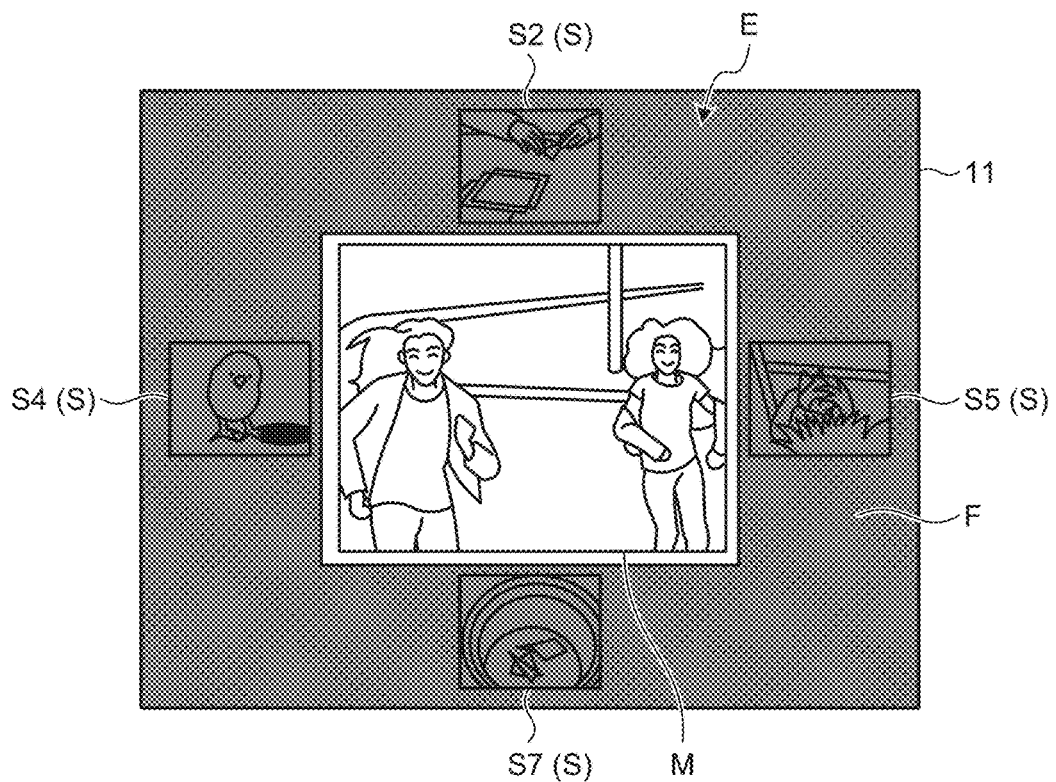
FIG. 7 is a diagram illustrating the display transition of the evaluation image.
Figure 8:
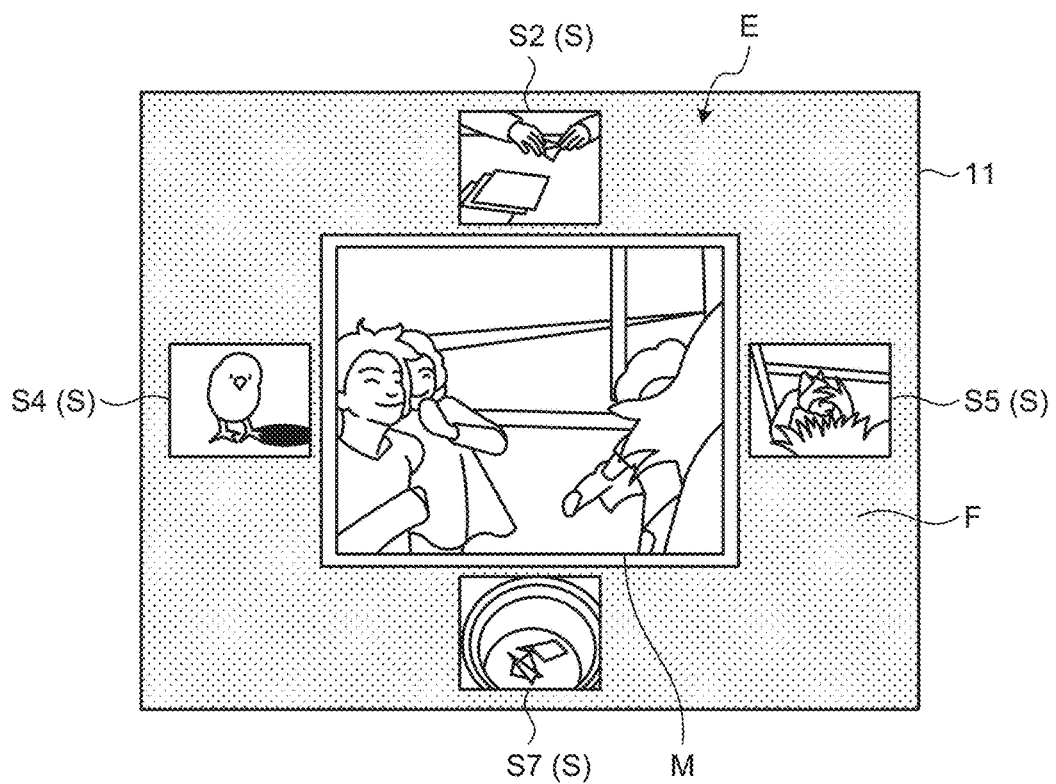
FIG. 8 is a diagram illustrating the display transition of the evaluation image.

From this state, as illustrated in FIG. 7, the display control unit 31 gradually reduces the transparency of some (S2, S4, S5, S7) of the sub target images S and the frame portion F with time such that some of the sub target images S can be are gradually recognized. Then, as illustrated in FIG. 8, when the transparency of some of the sub target images S2, S4, S5, S7 and the frame portion F reach 0%, display states of some of the sub target images S2, S4, S5, S7 and the display state of the frame portion F become the same as the display state of the main target image M.

Figure 9:
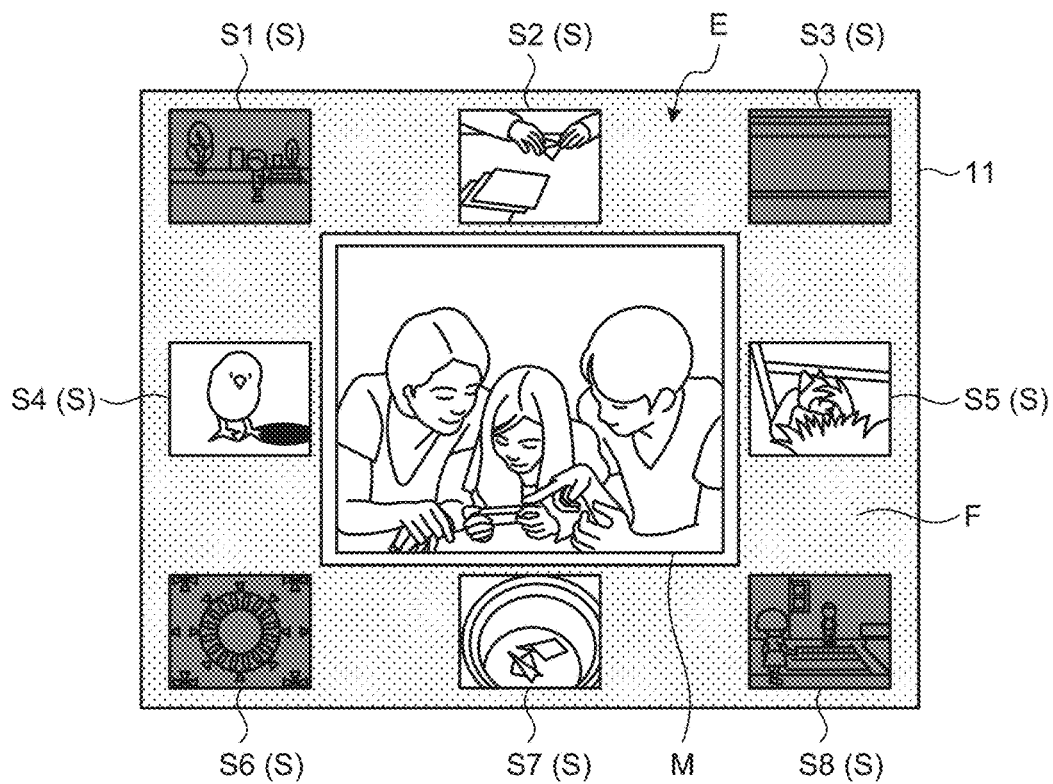
FIG. 9 is a diagram illustrating the display transition of the evaluation image.
Figure 10:
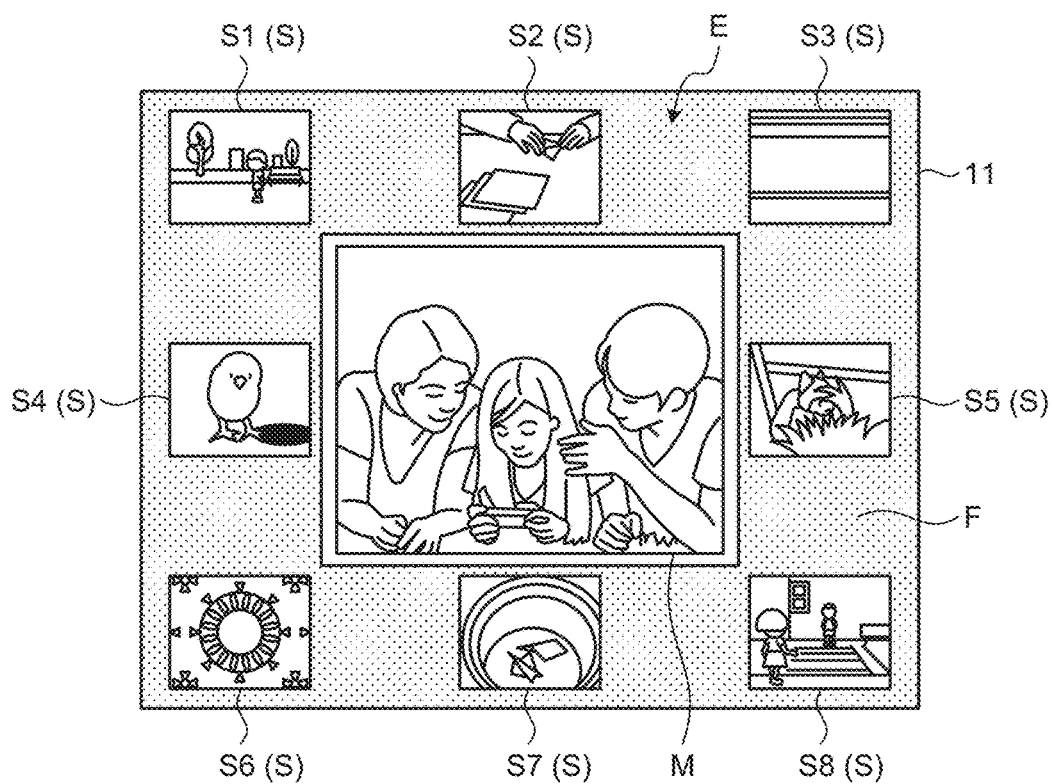
FIG. 10 is a diagram illustrating the display transition of the evaluation image.

Thereafter, as illustrated in FIG. 9, the display control unit 31 gradually reduces the transparency of the others of the sub target images S (S1, S3, S6, S8) with time such that the others of the sub target images S can be are gradually recognized. Then, as illustrated in FIG. 10, when the transparency of the others of the sub target images S1, S3, S6, and S8 reach 0%, display states of the others of the sub target images SS1, S3, S6, and S8 becomes the same as the display state the main target image M, the display states of some of the sub target images S2, S4, S5, S7, and the display state of the frame portion F.

The gaze point detection unit 32 detects a position of the gaze point P of the subject for each prescribed sampling cycle (for example, 20 (msec)) for the display period of the evaluation image E. When the position of the gaze point P of the subject is detected, the determination unit 34 determines whether the gaze point of the subject is present in the determination regions A1 to A8, and outputs a determination data. Therefore, the determination unit 34 outputs the determination data for each determination cycle that is the same as the sampling cycle as described above, every time the gaze point detection unit 32 performs the sampling of the position of the gaze point.

The arithmetic unit 35 calculates the arrival time of the first arrival of the gaze point at the determination region based on the determination data indicating whether the gaze point is present in the determination regions. The arrival time is a time from the predetermined time to a time at which the gaze point first arrives at each of the determination regions A1 to A8. The arithmetic unit 35 calculates the arrival time by the timer. The arithmetic unit 35 is able to adopt, as the predetermined time as the start point for the calculation of the arrival time, a time at which the display of the evaluation image E is started after the instruction information I is provided, for example. Further, when the specific region B for the main target image M is set (see FIG. 5), the arithmetic unit 35 may adopt, as the predetermined time, a time at which the gaze point of the subject is first confirmed to be present in the specific region B. When the multiple determination regions A1 to A8 are set as in the present embodiment, the arithmetic unit 35 calculates the arrival time for each of the determination regions.

The evaluation unit 36 obtains an evaluation value based on the arrival time of the gaze point, and obtains an evaluation data based on the evaluation value. In the present embodiment, assuming that the arrival times at the determination regions A1 to A8 are denoted by t1 to t8 for example, the evaluation unit 36 is able to obtain an evaluation value ANS as follows.

$$ANS=(t1+t2+t3+t4+t5+t6+t7+t8)/8$$

In other words, the evaluation value ANS is an average value of the arrival times t1 to t8. Meanwhile, when the gaze point does not arrive at the determination regions A during the display period of the evaluation image E, the values t1 to t8 may be times for the display period, for example. Meanwhile, the evaluation unit 36 may adopt, as the evaluation value ANS, a total value of the arrival times t1 to t8 of the determination regions A1 to A8.

The evaluation unit 36 is able to obtain the evaluation data by determining whether a value of the evaluation value ANS is equal to or larger than a predetermined threshold K. For example, when the evaluation value ANS is equal to or larger than the threshold K, it is determined that the gaze point is moved with a temporal delay or the gaze point is not moved, and it is possible to evaluate that the probability that the subject has ADHD is low. Further, when the evaluation value ANS is smaller than the threshold K, it is determined that the gaze point is moved at an early stage, and it is possible to evaluate that the probability that the subject has ADHD is high.

Furthermore, the evaluation unit 36 is able to store the value of the evaluation value ANS in the storage 38. For example, it may be possible to cumulatively store the evaluation values ANS with respect to the same subject, and perform evaluation by comparison with past evaluation values. For example, when the evaluation value ANS has a higher value than the past evaluation values, it is possible to evaluate that the symptoms of ADHD are improved as compared to the previous evaluation. Further, when the cumulative values of the evaluation value ANS are gradually increased for example, it is possible to evaluate that the symptoms of ADHD are gradually improved.

In the present embodiment, when the evaluation unit 36 outputs the evaluation data, the input-output control unit 37 is able to cause the output device 40 to output character data indicating that "the probability that the subject has ADHD is low", character data indicating that "the probability that the subject has ADHD is high", or the like in accordance with the evaluation data, for example. Further, when the evaluation value ANS with respect to the same subject is reduced as compared to the past evaluation values ANS, the input-output control unit 37 is able to cause the output device 40 to output character data indicating that "symptoms of ADHD are improved" or the like.

Figure 11:
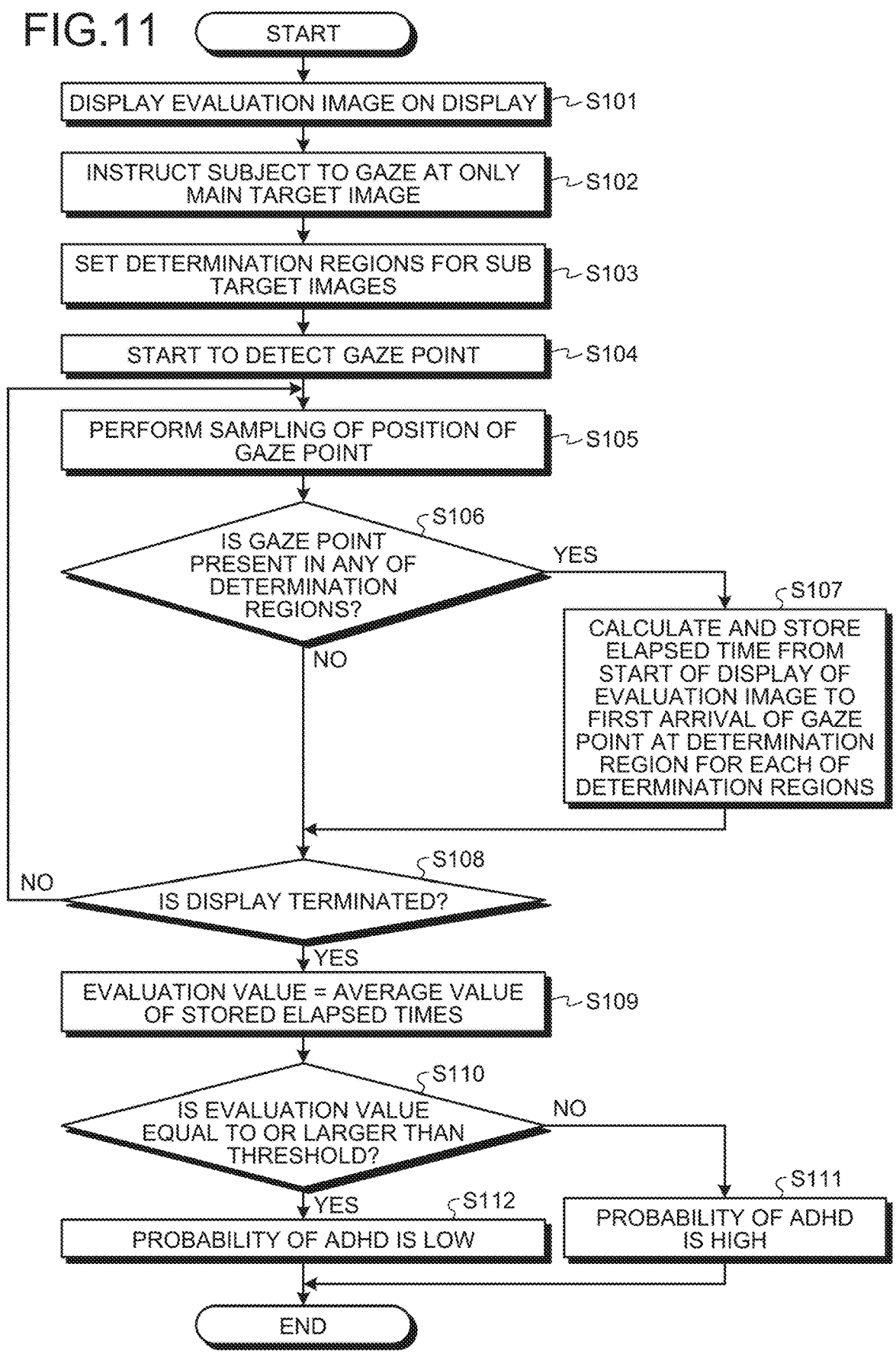
FIG. 11 is a flowchart illustrating an example of an evaluation method according to the present embodiment.

An example of the evaluation method according to the present embodiment will be described below with reference to FIG. 11. FIG. 11 is a flowchart illustrating an example of the evaluation method according to the present embodiment. In the evaluation method according to the present embodiment, as illustrated in FIG. 11, the display control unit 31 first displays the evaluation image E on the display 11 (Step S101). Subsequently, the display control unit 31 displays the instruction information I indicating an instruction to gaze at only the main target image M in the evaluation image E on the display 11 (Step S102).

Thereafter, the display control unit 31 terminates the display of the instruction information I, and displays the evaluation image E on the display 11. Further, the region setting unit 33 sets the determination regions A (A1 to A8) for the sub target images S in the evaluation image E (Step S103). Thereafter, the gaze point detection unit 32 starts to detect the gaze point (Step S104).

The gaze point detection unit 32 performs sampling of the position of the gaze point with a predetermined sampling cycle (Step S105). The determination unit 34 determines, with respect to the gaze point, whether the gaze point is present in each of the determination regions A1 to A8 every time the gaze point detection unit 32 performs the sampling of the position of the gaze point, and outputs the determination data (Step S106). When it is determined that the gaze point is present in any of the determination regions A1 to A8 (Yes at Step S106), the arithmetic unit 35 calculates, as the arrival time, an elapsed time from the start of the display of the evaluation image E to the first arrival time of the gaze point for each of the determination regions A1 to A8, based on the determination data (Step S107). When the process at Step S107 is performed or when it is determined that the gaze point is not present in any of the determination regions A1 to A8 (No at Step S106), the arithmetic unit 35 determines whether the display of the evaluation image E is terminated (Step S108). When it is determined that the display is not terminated (No at Step S108), the processes from Step S105 are performed. When it is determined that the display is terminated (Yes at Step S108), the evaluation unit 36 obtains, as the evaluation value (ANS), an average value of the calculated arrival times of the first arrival of the gaze point at each of the determination regions (Step S109).

The evaluation unit 36 determines whether the evaluation value (ANS) is equal to or larger than the threshold (K) (Step S110). When the evaluation value (ANS) is not equal to or larger than (i.e., is smaller than) the threshold (K) (No at Step S110), the evaluation unit 36 determines that the gaze point is moved at an early stage, evaluates that the probability that the subject has ADHD is high (Step S111), and terminates the process. When the evaluation value is equal to or larger than the threshold (Yes at Step S110), the evaluation unit 36 determines that the gaze point is moved with a temporal delay or the gaze point is not moved, evaluates that the probability that the subject has ADHD is low (Step S112), and terminates the process.

As described above, the evaluation apparatus 100 according to the present embodiment includes the display 11; the gaze point detection unit 32 configured to detect a position of a gaze point of a subject; the display controller configured to display, on the display 11, an evaluation image E including a main target image M, multiple images S, and an instruction information I for instructing the subject to gaze at the main target image M; the region setting unit 33 configured to set multiple determination regions A for the multiple sub target images S; the determination unit 34 configured to determine whether the gaze point is present in each of the multiple determination regions A based on the detected position of the gaze point; the arithmetic unit 35 configured to measure an arrival time from a predetermined time to a first arrival time of the gaze point at each of the multiple determination regions A based on a determination result of the determination unit 34; and an evaluation unit 36 configured to obtain an evaluation data of the subject based on the arrival time.

The evaluation method according to the present embodiment includes detecting a position of a gaze point of a subject; displaying, on a display 11, an evaluation image E including a main target image M, multiple sub target images S, and an instruction information I for instructing the subject to gaze at the main target image M; setting multiple determination regions A for the multiple sub target images S; determining whether the gaze point is present in each of the multiple determination regions A based on the detected position of the gaze point; measuring an arrival time from a predetermined time to a first arrival time of the gaze point at each of the multiple determination regions A based on a determination result of the determining; and obtaining an evaluation data of the subject based on the arrival time.

The non-transitory storage medium according to the present embodiment stores an evaluation program causes a computer to execute a process of detecting a position of a gaze point of a subject; a process of displaying, on a display 11, an evaluation image E including a main target image M, multiple sub target images S, and an instruction information I for instructing the subject to gaze at the main target image M; a process of setting multiple determination regions A for the multiple sub target images S; a process of determining whether the gaze point is present in each of the multiple determination regions A based on the detected position of the gaze point; a process of measuring an arrival time from a predetermined time to a first arrival time of the gaze point at each of the multiple determination regions A based on a determination result of the determining; and a process of obtaining an evaluation data of the subject based on the arrival time.

A subject with ADHD, even when the subject is instructed to gaze at a predetermined region for example, tends to move the gaze point to a different region other than the predetermined region at an early stage after the start of the evaluation, due to hyperactivity or impulsivity. Therefore, according to the present embodiment, after giving the instruction to gaze at the main target image M, the sub target images S that attract the attention of the subject are displayed, the arrival time of the first arrival at each of the determination regions for the sub target images S is measured, and the subject is evaluated based on the measured arrival times. With this configuration, it is possible to perform an evaluation that is directly suitable for the characteristics specific to the subject with ADHD.

In the evaluation apparatus 100 according to the present embodiment, the display control unit 31 changes the evaluation image from a state in which the sub target images S can hardly be recognized by the subject to a state in which the sub target images S can easily be recognized by the subject with time, and allows the subject to recognize the sub target images S with a delay from the main target image M. With this configuration, it is possible to easily generate a time lag between the display of the main target image M and the display of the sub target images S.

In the evaluation apparatus 100 according to the present embodiment, the region setting unit 33 sets the specific region B for the main target image M, the determination unit 34 determines whether the gaze point is present in the specific region B based on the position of the gaze point, and the arithmetic unit 35 adopts, as the start point for the calculation of the arrival time, a time at which the gaze point is determined to be first present in the specific region B. With this configuration, counting of the arrival time of the first arrival of the gaze point at the determination regions A is started from the state in which the subject gazes at the main target image M, so that it is possible to reliably perform the evaluation from the state in which the instruction indicated by the instruction information I is met. Therefore, it is possible to obtain a result with high accuracy.

In the evaluation apparatus 100 according to the present embodiment, the multiple sub target images S are arranged, the region setting unit 33 sets the determination regions A for each of the sub target images S, the arithmetic unit 35 measures the arrival time of the gaze point for each of the determination regions A, and the evaluation unit 36 obtains the evaluation data based on the average value of the arrival times. With this configuration, for example, it is possible to reduce an influence of a case in which the subject who does not have ADHD gazes at the sub target images S by mistake.

The technical scope of the present disclosure is not limited to the embodiments as described above, and modifications may be appropriately made without departing from the gist of the present disclosure. For example, in each of the embodiments as described above, the example has been described in which the evaluation apparatus 100 is used as an evaluation apparatus that evaluates the probability of ADHD, but the present disclosure is not limited to this example. For example, the evaluation apparatus 100 may be used as an evaluation apparatus that performs evaluation on other probability, such as evaluation on probability of cognitive impairment and brain impairment or evaluation of visual cognitive functions, other than the probability of ADHD.

According to the present disclosure, it is possible to perform evaluation that is directly suitable for the characteristics specific to the subject with ADHD.

Although the application has been described with respect to specific embodiments for a complete and clear application, the appended claims are not to be thus limited but are to be construed as embodying all modifications and alternative constructions that may occur to one skilled in the art that fairly fall within the basic teaching herein set forth.

What is claimed is:

1. An evaluation apparatus comprising:
    a display;
    a gaze point detection unit configured to detect a position of a gaze point of a subject;
    a display controller configured to display, on the display, an evaluation image including a main target image, multiple sub target images, and an instruction information for instructing the subject to gaze at the main target image;
    a region setting unit configured to set multiple determination regions for the multiple sub target images respectively;
    a determination unit configured to determine whether the gaze point is present in each of the multiple determination regions based on the detected position of the gaze point;
    an arithmetic unit configured to measure an arrival time from a predetermined time to a first arrival time of the gaze point at each of the multiple determination regions based on a determination result of the determination unit; and
    an evaluation unit configured to evaluate that probability that the subject has attention deficit hyperactivity disorder is classified as high when an average value or a total value of all of the arrival times for all of the multiple determination regions is smaller than a predetermined threshold value as compared with the probability when the average value or the total value of all of the arrival times for all of the multiple determination regions is at or larger than the predetermined threshold value.

2. The evaluation apparatus according to claim 1, wherein the display controller changes the evaluation image from a state in which the multiple sub target images are hardly able to be recognized by the subject to a state in which the multiple sub target images are easily able to be recognized by the subject.

3. The evaluation apparatus according to claim 2, wherein
    the region setting unit is further configured to set a specific region for the main target image,
    the determination unit is further configured to determine whether the gaze point is present in the specific region based on the position of the gaze point, and
    the arithmetic unit is further configured to adopt, as the predetermined time, a time at which the gaze point is first determined to be present in the specific region.

4. The evaluation apparatus according to claim 1, wherein
    the region setting unit is further configured to set a specific region for the main target image,
    the determination unit is further configured to determine whether the gaze point is present in the specific region based on the position of the gaze point, and
    the arithmetic unit is further configured to adopt, as the predetermined time, a time at which the gaze point is first determined to be present in the specific region.

5. An evaluation method comprising:
    detecting a position of a gaze point of a subject;
    displaying, on a display, an evaluation image including a main target image, multiple sub target images, and an instruction information for instructing the subject to gaze at the main target image;
    setting multiple determination regions for the multiple sub target images respectively;
    determining whether the gaze point is present in each of the multiple determination regions based on the detected position of the gaze point;
    measuring an arrival time from a predetermined time to a first arrival time of the gaze point at each of the multiple determination regions based on a determination result of the determining; and
    evaluating that probability that the subject has attention deficit hyperactivity disorder is classified as high when an average value or a total value of all of the arrival times for all of the multiple determination regions is smaller than a predetermined threshold value as compared with the probability when the average value or the total value of all of the arrival times for all of the multiple determination regions is at or larger than the predetermined threshold value.

6. A non-transitory storage medium that stores an evaluation program that causes a computer to execute:
- a process of detecting a position of a gaze point of a subject;
- a process of displaying, on a display, an evaluation image including a main target image, multiple sub target images, and an instruction information for instructing the subject to gaze at the main target image;
- a process of setting multiple determination regions for the multiple sub target images respectively;
- a process of determining whether the gaze point is present in each of the multiple determination regions based on the detected position of the gaze point;
- a process of measuring an arrival time from a predetermined time to a first arrival time of the gaze point at each of the multiple determination regions based on a determination result of the determining; and
- a process of evaluating that probability that the subject has attention deficit hyperactivity disorder is classified as high when an average value or a total value of all of the arrival times for all of the multiple determination regions is smaller than a predetermined threshold value as compared with the probability when the average value or the total value of all of the arrival times for all of the multiple determination regions is at or larger than the predetermined threshold value.

* * * * *